United States Patent
Liu et al.

(10) Patent No.: US 6,969,900 B2
(45) Date of Patent: Nov. 29, 2005

(54) SEMICONDUCTOR DIODE CAPABLE OF DETECTING HYDROGEN AT HIGH TEMPERATURES

(75) Inventors: Wen-Chau Liu, Tainan (TW); Huey-Ing Chen, Tainan (TW); Kun-Wei Lin, Tou-Liu (TW); Chun-Tsen Lu, Hsin-Tien (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 10/797,863

(22) Filed: Mar. 10, 2004

(65) Prior Publication Data

US 2004/0183153 A1   Sep. 23, 2004

Related U.S. Application Data

(63) Continuation-in-part of application No. 10/725,801, filed on Dec. 2, 2003.

(30) Foreign Application Priority Data

Mar. 17, 2003   (TW) ................................ 92105825 A (51) Int. Cl.$^7$ ............................................. G01N 27/00
(52) U.S. Cl. ................... 257/485; 257/472; 257/473; 422/82.03
(58) Field of Search ................................ 257/252–253, 257/414, 453, 472–473, 485; 422/82.01, 422/82.02, 82.03, 82.04; 436/144

(56) References Cited

U.S. PATENT DOCUMENTS

| | | | | |
|---|---|---|---|---|
| 4,058,368 A | * | 11/1977 | Svensson et al. | 422/88 |
| 4,892,834 A | * | 1/1990 | Rauh | 436/149 |
| 5,060,030 A | * | 10/1991 | Hoke | 257/194 |
| 5,949,096 A | * | 9/1999 | Ohkubo et al. | 257/192 |
| 6,160,278 A | * | 12/2000 | Liu et al. | 257/252 |

* cited by examiner

*Primary Examiner*—Minhloan Tran
*Assistant Examiner*—Thomas L. Dickey
(74) *Attorney, Agent, or Firm*—Ohlandt, Greeley, Ruggiero & Perle, L.L.P.

(57) ABSTRACT

A semiconductor diode with hydrogen detection capability includes a semiconductor substrate, a doped semiconductor active layer formed on the substrate and made from a compound having the formula XYZ, in which X is a Group III element, Y is another Group III element different from X, and Z is a Group V element, a semiconductor contact-enhancing layer formed on the active layer and made from a compound having the formula MN, in which M is a Group III element, and N is a Group V element, an ohmic contact layer formed on the semiconductor contact-enhancing layer, and a Schottky barrier contact layer formed on the active layer. The Schottky barrier contact layer is made from a metal that is capable of dissociating a hydrogen molecule into hydrogen atoms.

25 Claims, 7 Drawing Sheets

SEMICONDUCTOR DIODE CAPABLE OF DETECTING HYDROGEN AT HIGH TEMPERATURES

CROSS-REFERENCE TO RELATED APPLICATION

This application is a continuation-in-part (CIP) of co-pending U.S. patent application Ser. No. 10/725,801, filed by the applicant on Dec. 2, 2003, and claims priority of Taiwanese application No. 092105825, filed on Mar. 17, 2003.

BACKGROUND OF THE INVENTION

1. Field of the Invention

This invention relates to a semiconductor diode, more particularly to a semiconductor diode that is capable of detecting hydrogen at high temperatures.

2. Description of the Related Art

In co-pending U.S. patent application Ser. No. 10/725,801, the applicant disclosed a semiconductor diode with hydrogen detection capability. The semiconductor diode includes: a semiconductor substrate; a doped semiconductor active layer formed on the substrate and made from a compound having the formula XYZ, in which X is a Group m element, Y is another Group III element different from X, and Z is a Group V element; an ohmic contact layer formed on the active layer; and a Schottky barrier contact layer formed on the active layer so as to provide a Schottky barrier therebetween. The Schottky barrier contact layer is made from a metal that is capable of dissociating a hydrogen molecule into hydrogen atoms. The active layer is preferably made from n-type InGaP or $Al_xGa_{1-x}As$ so as to impart the semiconductor diode with a capability of detecting hydrogen at high temperatures.

However, due to a relatively large difference in surface property between the ohmic contact and the active layer, the contact therebetween is relatively poor, which results in an increase in the electrical resistance of the semiconductor diode.

The whole disclosure of the co-pending U.S. patent application Ser. No. 10/725,801 is incorporated herein by reference.

SUMMARY OF THE INVENTION

Therefore, the object of the present invention is to provide a semiconductor diode for hydrogen detection that is capable of overcoming the aforesaid drawback associated with the co-pending U.S. patent application Ser. No. 10/725,801.

According to the present invention, there is provided a semiconductor diode with hydrogen detection capability that includes: a semiconductor substrate; a doped semiconductor active layer formed on the substrate and made from a compound having the formula XYZ, in which X is a Group m element, Y is another Group III element different from X, and Z is a Group V element; a semiconductor contact-enhancing layer formed on the active layer and made from a compound having the formula MN, in which M is a Group III element, and N is a Group V element; an ohmic contact layer formed on the semiconductor contact-enhancing layer and extending through the semiconductor contact-enhancing layer and into the active layer; and a Schottky barrier contact layer formed on the active layer so as to provide a Schottky barrier therebetween. The Schottky barrier contact layer is made from a metal that is capable of dissociating a hydrogen molecule into hydrogen atoms.

BRIEF DESCRIPTION OF THE DRAWINGS

In drawings which illustrate an embodiment of the invention.

DETAILED DESCRIPTION OF THE PREFERRED EMBODIMENT

Figure 1:
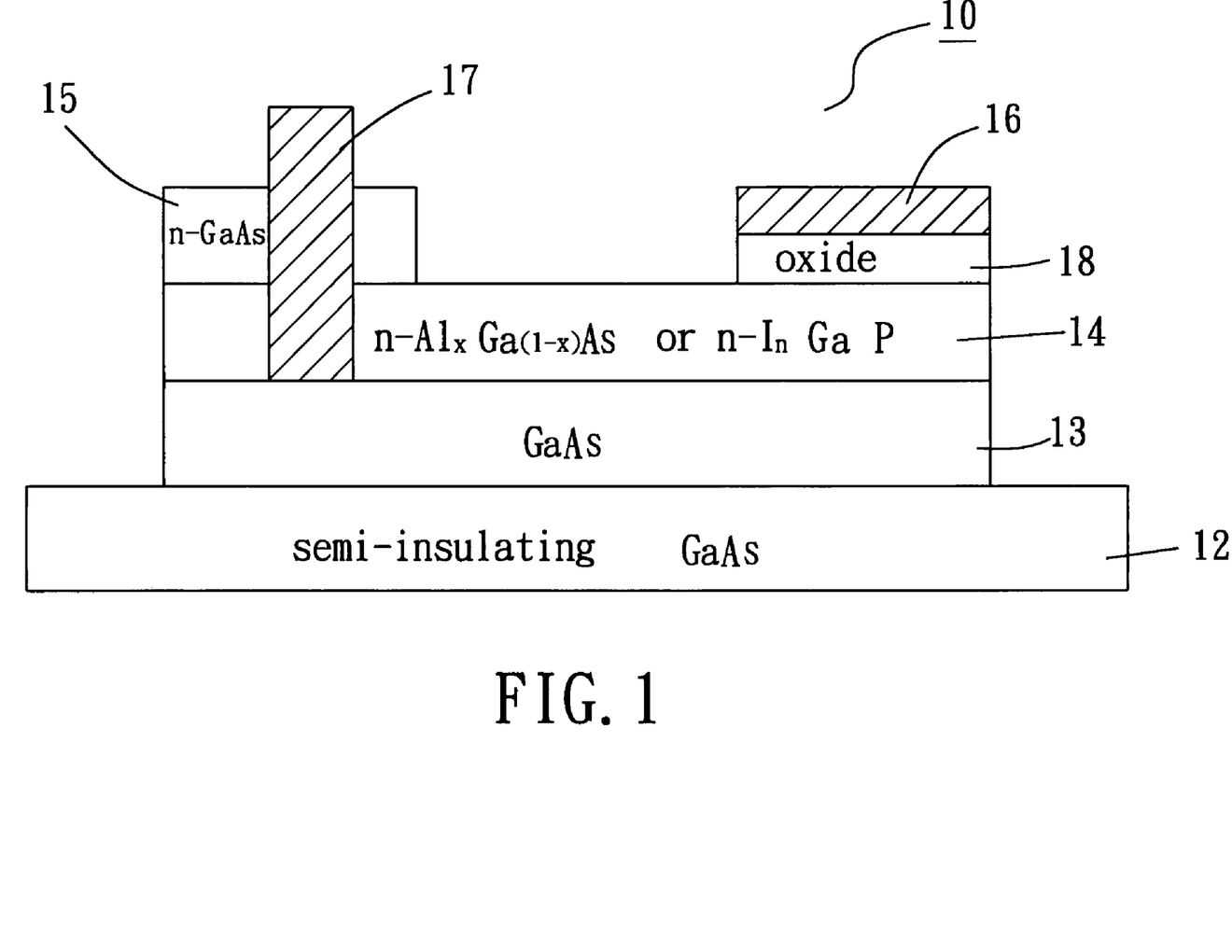
FIG. 1 is a schematic partly sectional view of the preferred embodiment of a semiconductor diode according to the present invention for detecting the presence of hydrogen.

FIG. 1 illustrates the preferred embodiment of a semiconductor diode 10 suitable for use in a hydrogen sensor according to the present invention. The semiconductor diode 10 includes: a semiconductor substrate 12; a doped semiconductor active layer 14 formed on the substrate 12 and made from a compound having the formula XYZ, in which X is a Group III element, Y is another Group m element different from X, and Z is a Group V element; a semiconductor contact-enhancing layer 15 formed on the active layer 14 and made from a compound having the formula MN, in which M is a Group III element, and N is a Group V element; an ohmic contact layer 17 formed on the semiconductor contact-enhancing layer 15 and extending through the semiconductor contact-enhancing layer 15 and into the active layer 14; and a Schottky barrier contact layer 16 formed on the active layer 14 so as to provide a Schottky barrier therebetween. The Schottky barrier contact layer 16 is made from a metal that is capable of dissociating a hydrogen molecule into hydrogen atoms. The ohmic contact layer 17 is formed using vapor deposition techniques, and is subsequently annealed under a temperature of about 400° C. for about one about minute so as to permit extension thereof into the active layer 14.

Preferably, the semiconductor contact-enhancing layer 15 is made from n-GaAs, has a dopant concentration ranging from $1\times10^{17}$ to $1\times10^{19}$ atoms/cm$^3$, and has a thickness ranging from 100 to 3000 Å.

Figure 2:
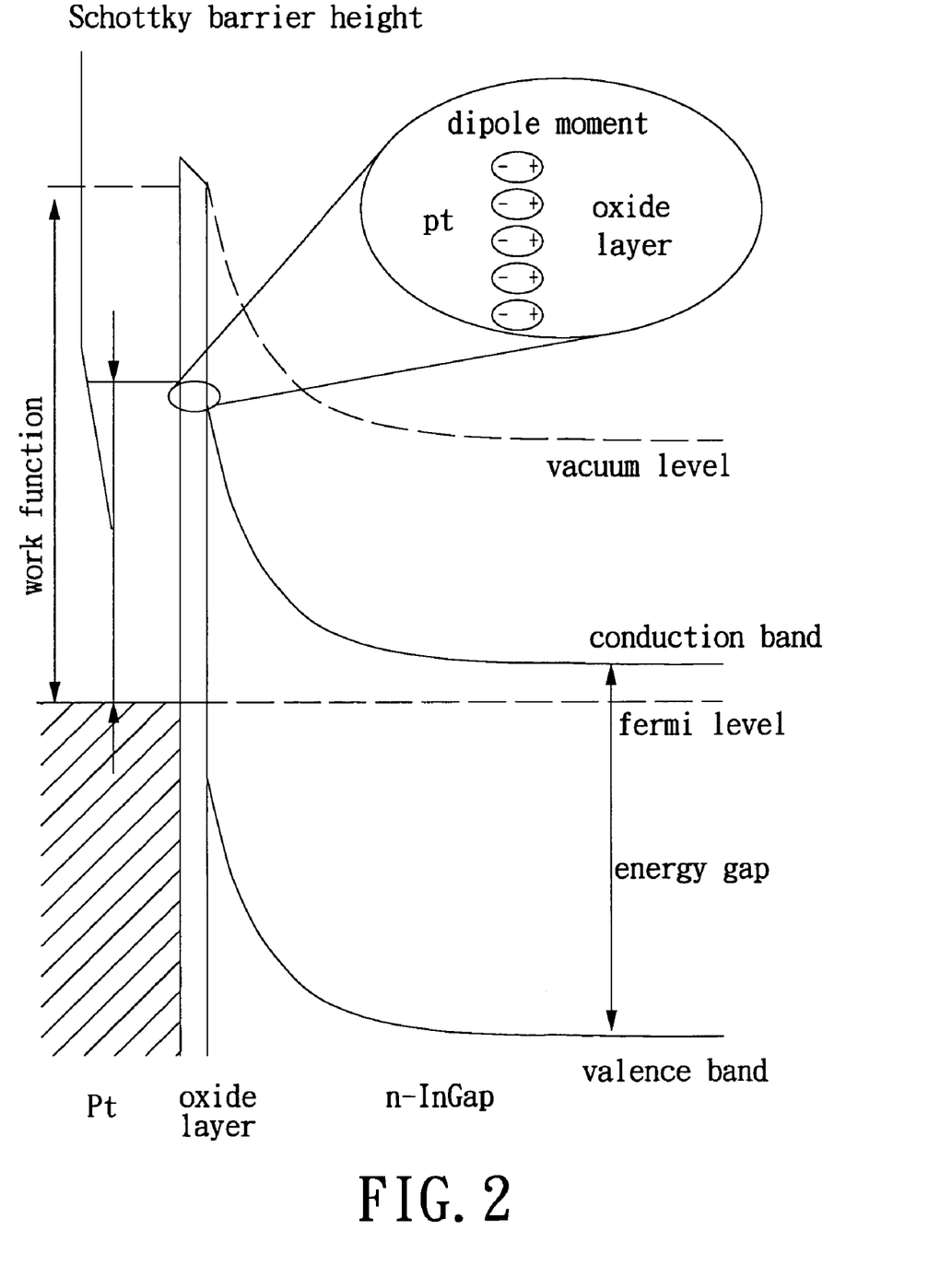
FIG. 2 is an energy band diagram showing the energy band of the preferred embodiment of this invention upon detecting the presence of hydrogen.

Preferably, an oxide layer 18 is sandwiched between the Schottky barrier contact layer 16 and the active layer 14. The hydrogen atoms thus formed diffuse through the Schottky barrier contact layer 16, and are trapped in the junction between the Schottky barrier contact layer 16 and the oxide layer 18, which results in the formation of a dipole moment layer (see FIG. 2) therebetween, which, in turn, results in an unbalance in the charge distribution therebetween. The aforesaid charge distribution reaches a new equilibrium state when the hydrogen atoms cease to diffuse through the Schottky barrier contact layer 16. The dipole moment layer reduces the width of the depletion region of the active layer 14 and the Schottky barrier of the Schottky barrier contact layer 16.

The oxide layer 18 serves to broaden the variation range of the Schottky barrier, which results in an increase in the sensitivity of the semiconductor diode 10. The oxide layer 18 is preferably made from a compound selected from the group consisting of silicone dioxide, titanium didoxide, and zinc oxide, and preferably has a thickness ranging from 20 to 500 Å.

Preferably, the compound of the active layer 14 is selected from the group consisting of n-type $In_{0.49}Ga_{0.51}P$ and $Al_xGa_{1-x}As$ with x=0–1. The active layer 14 preferably has a dopant concentration ranging from $1\times10^{15}$ to $5\times10^{18}$ atoms/cm$^3$, and a thickness ranging from 1000 to 5000 Å.

The substrate 12 is preferably made from semi-insulating GaAs. Preferably, a semiconductor buffer layer 13 is sandwiched between the substrate 12 and the active layer 14, is made from undoped i-GaAs, and has a thickness ranging from 1000 to 50000 Å.

Preferably, the ohmic contact layer 17 is made from AuGe/Ni or Au/Ge, and has a thickness ranging from 1000 to 50000 Å.

Preferably, the metal of the Schottky barrier contact layer 16 is selected from the group consisting of Pt, Pd, Ni, Rh, Ru, and Ir. The Schottky barrier contact layer 16 preferably has a thickness ranging from 100 to 20000 Å.

The present invention will now be described in greater detail in connection with the following test results.

FIGS. 3 to 7 show the test results of the preferred embodiment of the semiconductor diode 10 according to this invention.

Figure 3:
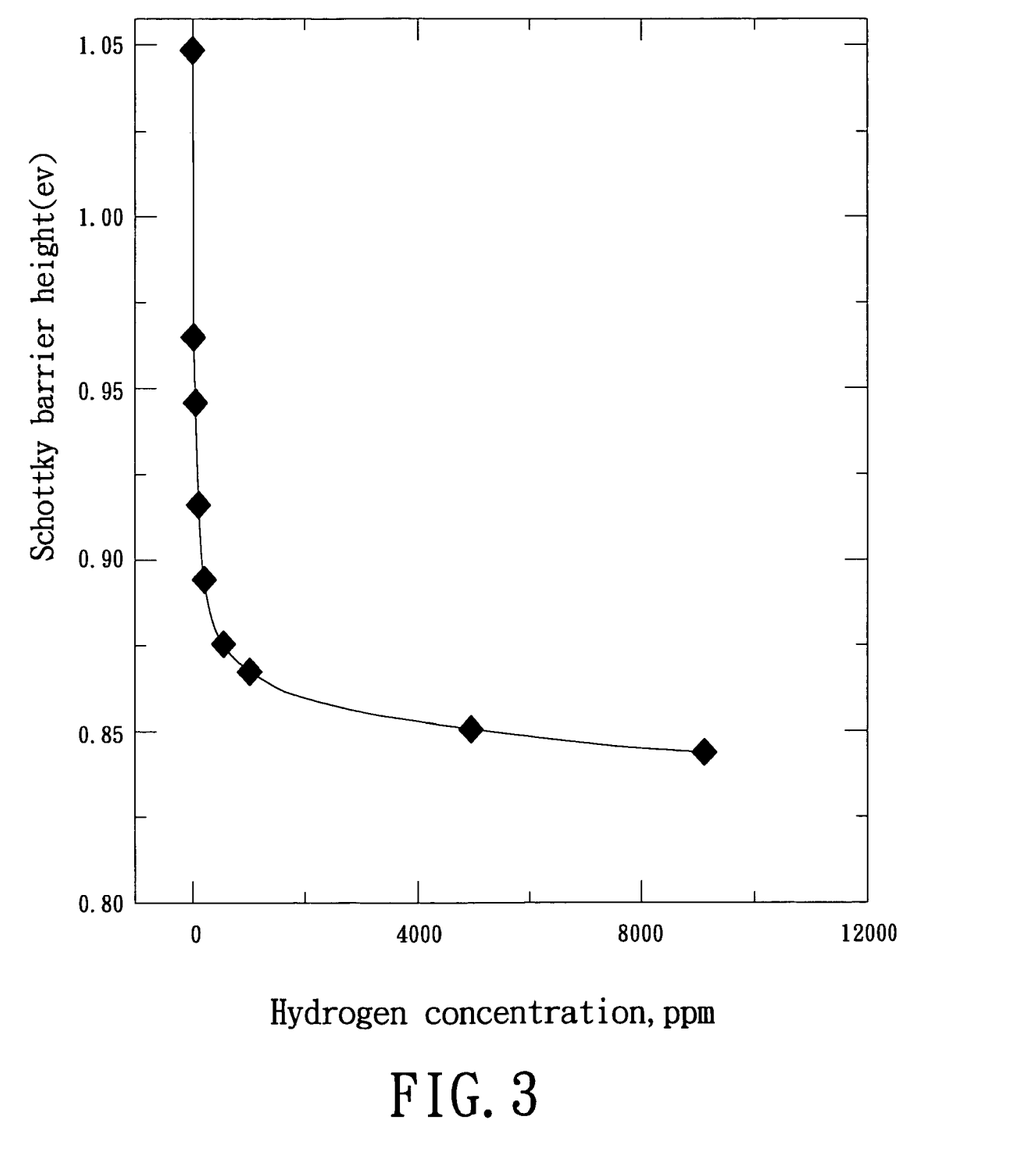
FIG. 3 is a diagram showing Schottky barrier heights of the preferred embodiment for different hydrogen concentrations.

FIG. 3 shows the Schottky barrier heights of the preferred embodiment for different hydrogen concentrations. The results indicate that the higher the hydrogen concentration, the lower will be the resultant Schottky barrier heights and that the Schottky barrier heights decreases sharply in an exponential order at a low hydrogen concentration region.

Figure 4:
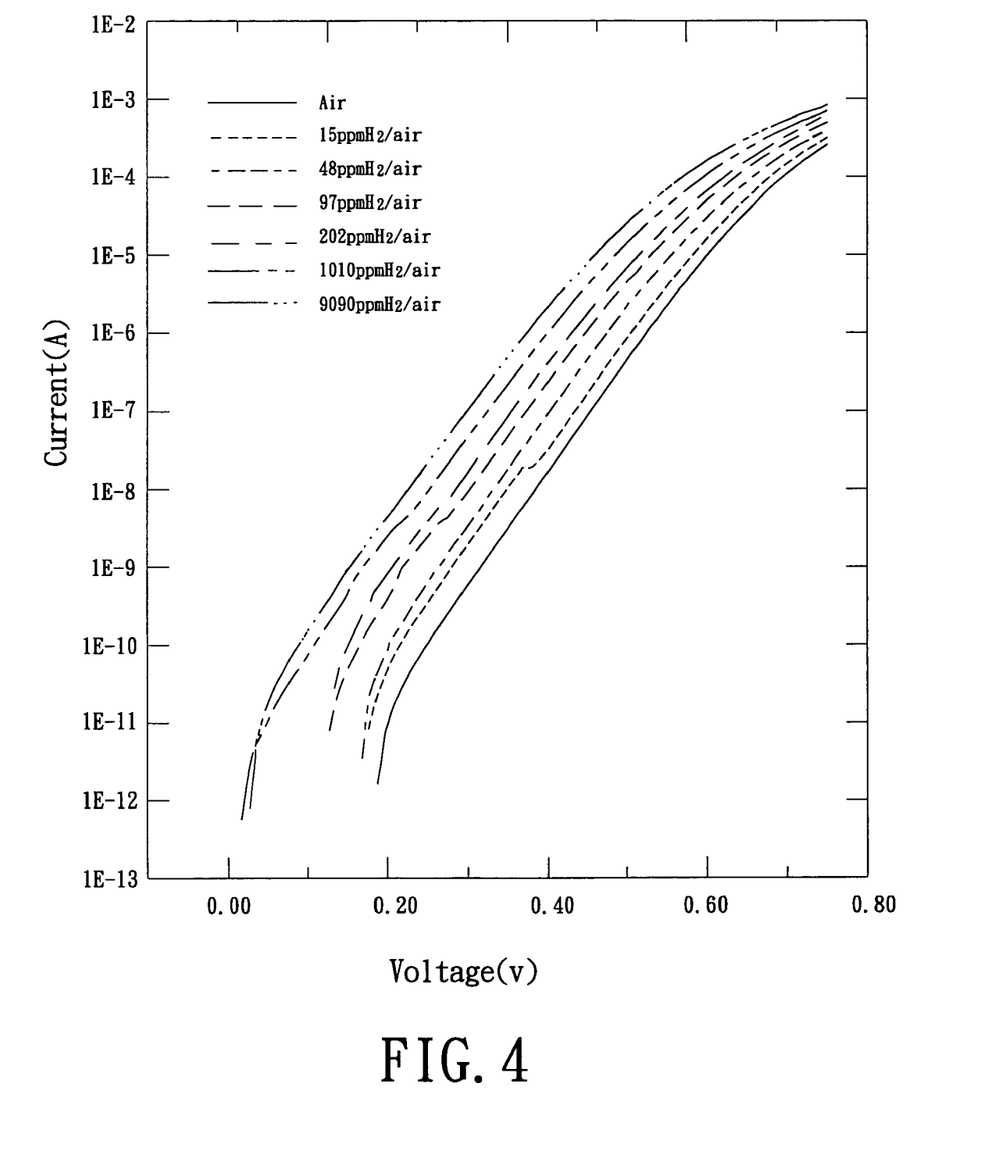
FIG. 4 is an I-V characteristics diagram showing I-V curves of the preferred embodiment during detection of hydrogen under different hydrogen concentrations.

FIG. 4 shows I-V curves (forward biased) obtained during hydrogen detection under different hydrogen concentrations (i.e., air, i.e., zero ppm, 15 ppm, 48 ppm, 97 ppm, 202 ppm, 1010 ppm, and 9090 ppm) and different biased voltages. The results indicate that the higher the hydrogen concentration, the higher will be the resultant electric current.

Figure 5:
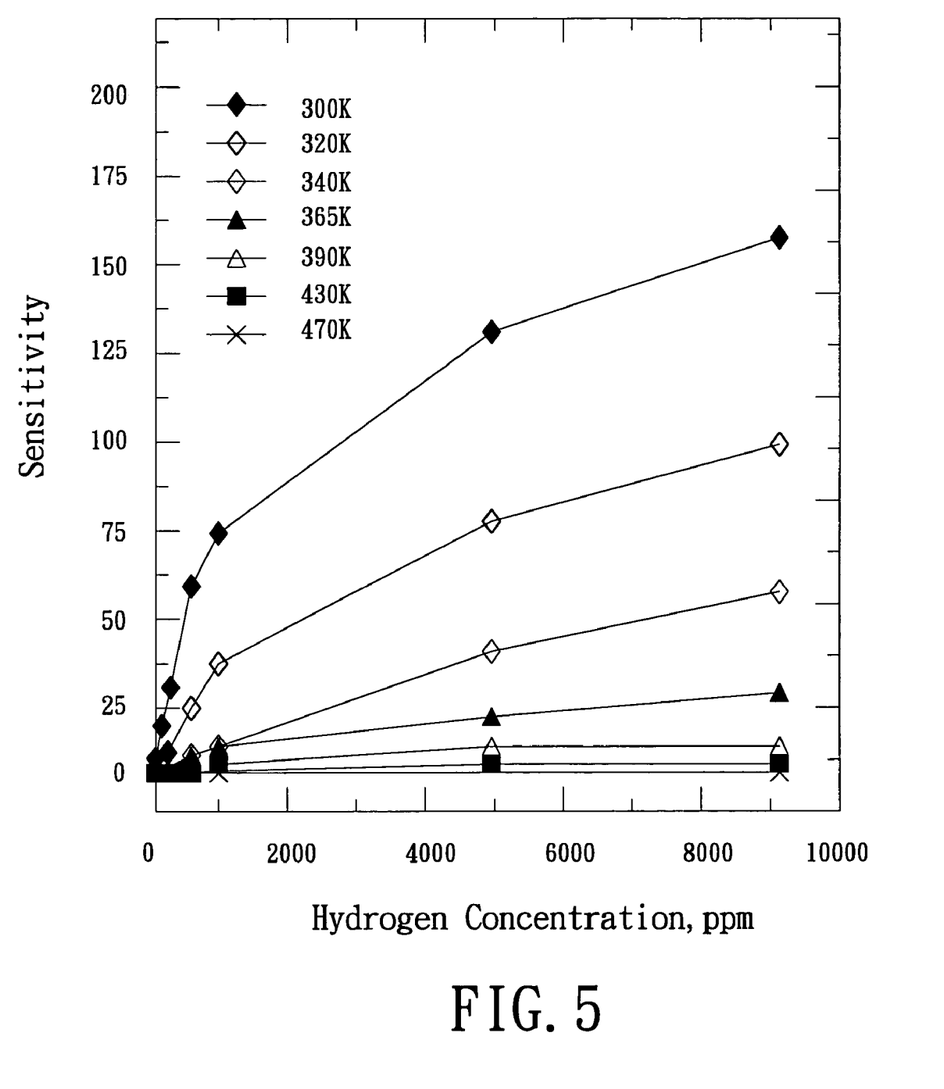
FIG. 5 is a sensitivity-vs-hydrogen concentration diagram showing the sensitivity of the preferred embodiment during detection of hydrogen under different hydrogen concentrations and detecting temperatures.

FIG. 5 shows measured sensitivity of the semiconductor diode 10 in detecting the presence of hydrogen under different detecting temperatures (i.e., 300K, 320K, 340K, 365K, 390K, 430K, and 470K) and under different hydrogen concentrations. The sensitivity (S) is defined as S(%)= $(I_h-I_a)/I_a$ (%), in which $I_h$ is the measured current in the presence of hydrogen in the air, and $I_a$ is the measured current without the presence of hydrogen in the air. The sensitivity test was conducted at a forward biased voltage of 0.35V. The results indicate that the higher the temperature, the lower will be the sensitivity for all the hydrogen concentrations, and that the higher the hydrogen concentration, the higher will be the sensitivity for all the detecting temperatures. Note that the increase in the sensitivity in FIG. 5 is particularly evident under temperatures above 365K.

Figure 6:
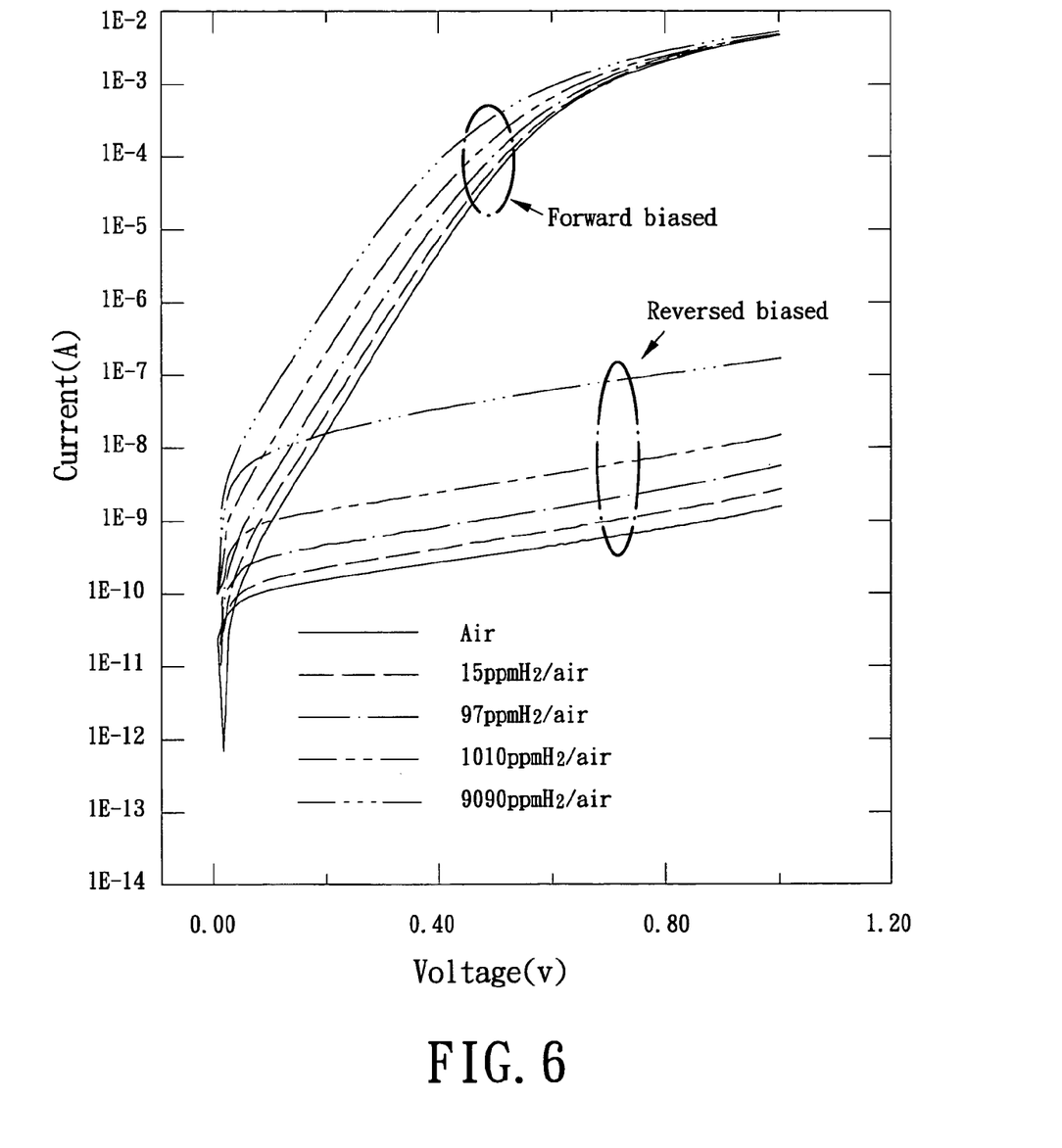
FIG. 6 is an I-V characteristics diagram showing I-V curves of the preferred embodiment during detection of hydrogen at a temperature of 95° C. under different hydrogen concentrations.

FIG. 6 shows I-V curves (forward and reverse biased voltages) of the preferred embodiment during detection of hydrogen at a temperature of 95° C. under different hydrogen concentrations (i.e., zero ppm, 15 ppm, 97 ppm, 1010 ppm, and 9090 ppm). The results indicate that the semiconductor diode 10 of this invention is capable of detecting hydrogen under a high temperature environment.

Figure 7:
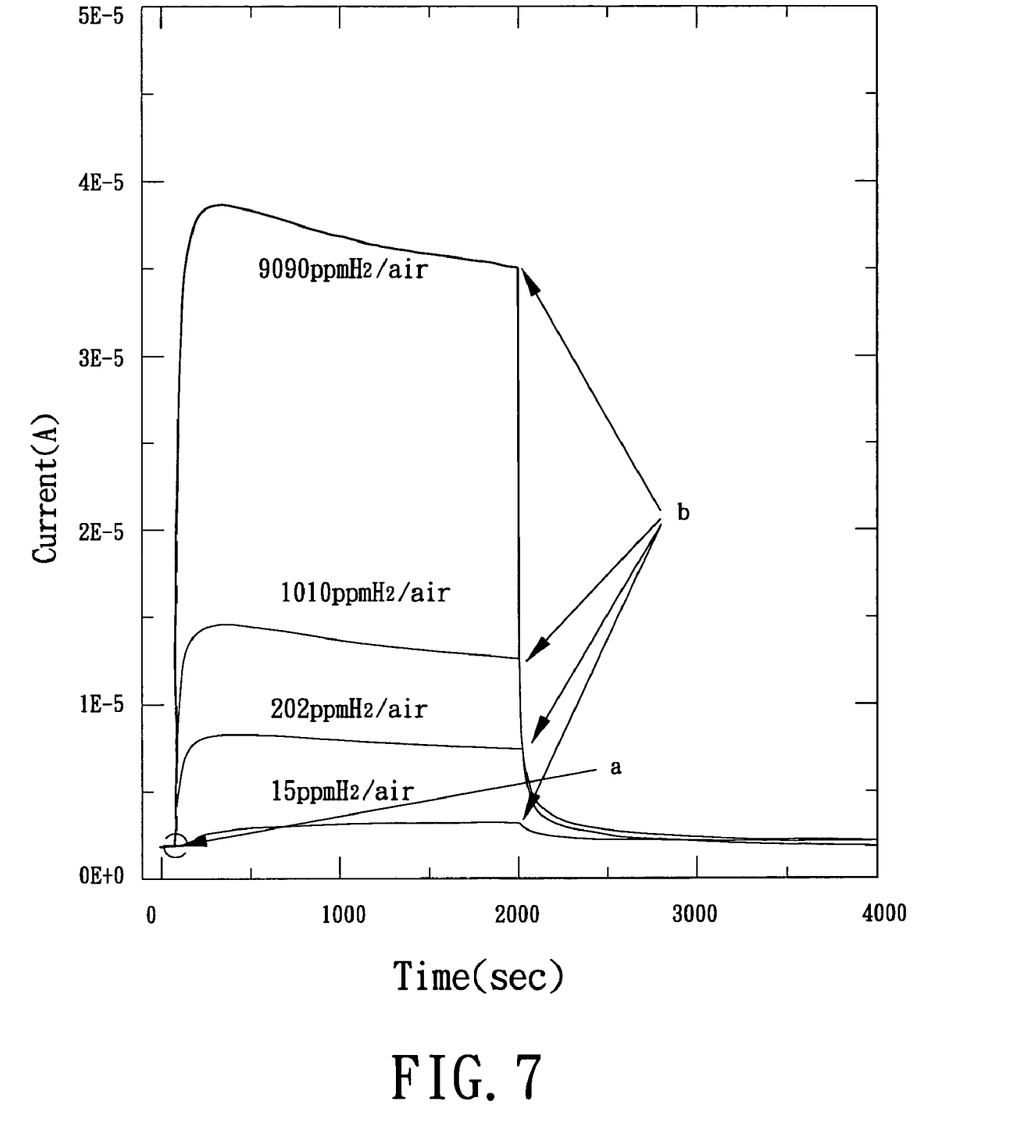
FIG. 7 is a diagram showing the response time of the preferred embodiment during detection of hydrogen under different hydrogen concentrations.

FIG. 7 shows the response time of the preferred embodiment during detection of hydrogen under different hydrogen concentrations. The response time of the semiconductor diode 10 was measured under a forward biased voltage of 0.35V at a temperature of 95° C. in a test chamber (not shown). The test chamber is connected to a hydrogen gas supply which supplies hydrogen into the test chamber in a rate of about 500 ml/min. The results show that the current rises steeply immediately after the hydrogen gas supply is turned on (indicated as reference mark "a" in FIG. 7) and drops sharply immediately after the hydrogen gas supply is turned off (indicated as reference mark "b" in FIG. 7). The hydrogen atoms trapped in the semiconductor diode 10 diffuse backward into the test chamber after the hydrogen gas supply is turned off, thereby resulting in recovery of electric current. The results indicate that the hydrogen-detecting semiconductor diode 10 has a response time of 302 seconds for 15 ppm hydrogen concentration, 40.3 seconds for 202 ppm hydrogen concentration, 13.2 seconds for 1010 ppm hydrogen concentration, and 4.5 seconds for 9090 ppm hydrogen concentration.

Compared to the semiconductor diode of the co-pending U.S. patent application Ser. No. 10/725,801, the semiconductor diode 10 of this invention exhibits a better surface contact between the ohmic contact 17 and the active layer 14. Moreover, the material used for the semiconductor contact-enhancing layer 15 imparts the semiconductor diode 10 with a better compatibility to connect or integrate with other electronic devices.

With the invention thus explained, it is apparent that various modifications and variations can be made without departing from the spirit of the present invention.

We claim:

1. A semiconductor diode with hydrogen detection capability, comprising:
   a semiconductor substrate;
   a doped semiconductor active layer formed on said substrate and made from a compound having the formula XYZ, in which X is a Group III element, Y is another Group III element different from X, and Z is a Group V element;
   a semiconductor contact-enhancing layer formed on said active layer and made from a compound having the formula MN, in which M is a Group III element, and N is a Group V element;
   an ohmic contact layer formed on said semiconductor contact-enhancing layer and extending through said semiconductor contact-enhancing layer and into said active layer;
   a Schottky barrier contact layer formed on said active layer so as to provide a Schottky barrier therebetween, said Schottky barrier contact layer being made from a metal that is capable of dissociating a hydrogen molecule into hydrogen atoms; and
   an oxide layer sandwiched between said active layer and said Schottky barrier contact layer.

2. The semiconductor diode of claim 1, wherein said semiconductor contact-enhancing layer is made from n-GaAs.

3. The semiconductor diode of claim 2, wherein said semiconductor contact-enhancing layer has a dopant concentration ranging from $1\times10^{17}$ to $1\times10^{19}$ atoms/cm$^3$.

4. The semiconductor diode of claim 3, wherein said semiconductor contact-enhancing layer has a thickness ranging from 100 to 3000 Å.

5. The semiconductor diode of claim 1, wherein said oxide layer is made from a compound selected from the group consisting of silicone dioxide titanium dioxide, and zinc oxide.

6. The semiconductor diode of claim 1, wherein said oxide layer has a thickness ranging from 20 to 500 Å.

7. The semiconductor diode of claim 1, wherein said compound of said active layer is selected from the group consisting of n-type InGaP and $Al_xGa_{1-x}As$.

8. The semiconductor diode of claim 7, wherein said compound of said active layer is n-type $In_{0.49}Ga_{0.51}P$ with a dopant concentration ranging from $1 \times 10^{15}$ to $5 \times 10^{18}$ atoms/$cm^3$, said active layer having a thickness ranging from 1000 to 5000 Å.

9. The semiconductor diode of claim 7, wherein said compound of said active layer is $Al_xGa_{1-x}As$ with x=0–1 and a dopant concentration ranging from $1 \times 10^{15}$ to $5 \times 10^{18}$ atoms/$cm^3$, said active layer having a thickness ranging from 1000 to 5000 Å.

10. The semiconductor diode of claim 1, further comprising a semiconductor buffer layer sandwiched between said substrate and said active layer.

11. The semiconductor diode of claim 10, wherein said buffer layer is made from undoped GaAs and has a thickness ranging from 1000 to 50000 Å.

12. The semiconductor diode of claim 1, wherein said substrate is made from semi-insulating GaAs.

13. The semiconductor diode of claim 1, wherein said ohmic contact layer is made from AuGe/Ni and has a thickness ranging from 1000 to 50000 Å.

14. The semiconductor diode of claim 1, wherein said ohmic contact layer is made from AuGe and has a thickness ranging from 1000 to 50000 Å.

15. The semiconductor diode of claim 1, wherein said metal of said Schottky barrier contact layer is selected from the group consisting of Pt, Pd, Ni, Rh, Ru, and Ir.

16. The semiconductor diode of claim 1, wherein said Schottky barrier contact layer has a thickness ranging from 100 to 20000 Å.

17. A semiconductor diode with hydrogen detection capability, comprising:
   a semiconductor substrate;
   a doped semiconductor active layer formed on said substrate and made from a compound having the formula XYZ, in which X is a Group III element, Y is another Group III element different from X, and Z is a Group V element;
   a semiconductor contact-enhancing layer formed on said active layer and made from a compound having the formula MN, in which M is a Group III element, and N is a Group V element;
   an ohmic contact layer formed on said semiconductor contact-enhancing layer and extending through said semiconductor contact-enhancing layer and into said active layer; and
   a Schottky barrier contact layer formed on said active layer so as to provide a Schottky barrier therebetween, said Schottky barrier contact layer being made from a metal that is capable of dissociating a hydrogen molecule into hydrogen atoms;
   wherein said compound of said active layer is selected from the group consisting of n-type InGaP and $Al_xGa_{1-x}As$; and
   wherein said compound of said active layer is n-type $In_{0.49}Ga_{0.51}P$ with a dopant concentration ranging from $1 \times 10^{15}$ to $5 \times 10^{18}$ atoms/$cm^3$, said active layer having a thickness ranging from 1000 to 5000 Å.

18. The semiconductor diode of claim 17, wherein said compound of said active layer is $Al_xGa_{1-x}As$ with x=0–1 and a dopant concentration ranging from $1 \times 10^{15}$ to $5 \times 10^{18}$ atoms/$cm^3$, said active layer having a thickness ranging from 1000 to 5000 Å.

19. The semiconductor diode of claim 17, further comprising a semiconductor buffer layer sandwiched between said substrate and said active layer.

20. The semiconductor diode of claim 19, wherein said buffer layer is made from undoped GaAs and has a thickness ranging from 1000 to 50000 Å.

21. The semiconductor diode of claim 17, wherein said substrate is made from semi-insulating GaAs.

22. The semiconductor diode of claim 17, wherein said ohmic contact layer is made from AuGe/Ni and has a thickness ranging from 1000 to 50000 Å.

23. The semiconductor diode of claim 17, wherein said ohmic contact layer is made from AuGe and has a thickness ranging from 1000 to 50000 Å.

24. The semiconductor diode of claim 17, wherein said metal of said Schottky barrier contact layer is selected from the group consisting of Pt, Pd, Ni, Rh, Ru, and Ir.

25. The semiconductor diode of claim 17, wherein said Schottky barrier contact layer has a thickness ranging from 100 to 20000 Å.

* * * * *